US010403895B2

(12) United States Patent
Pillow

(10) Patent No.: US 10,403,895 B2
(45) Date of Patent: Sep. 3, 2019

(54) ORGANIC FLOW CELL BATTERIES AND MATERIALS FOR USE IN SAME

(71) Applicant: Cambridge Display Technology Limited, Godmanchester (GB)

(72) Inventor: Jonathan Pillow, Hitchin (GB)

(73) Assignee: Cambridge Display Technology Limited, Godmanchester (GB)

( * ) Notice: Subject to any disclaimer, the term of this patent is extended or adjusted under 35 U.S.C. 154(b) by 49 days.

(21) Appl. No.: 15/539,414

(22) PCT Filed: Dec. 23, 2015

(86) PCT No.: PCT/EP2015/002607
§ 371 (c)(1),
(2) Date: Jun. 23, 2017

(87) PCT Pub. No.: WO2016/102069
PCT Pub. Date: Jun. 30, 2016

(65) Prior Publication Data
US 2018/0358621 A1    Dec. 13, 2018

Related U.S. Application Data

(60) Provisional application No. 62/095,832, filed on Dec. 23, 2014.

(51) Int. Cl.
*H01M 4/60*        (2006.01)
*C07D 209/04*      (2006.01)
(Continued)

(52) U.S. Cl.
CPC ............ *H01M 4/60* (2013.01); *C07D 209/04* (2013.01); *C07D 209/36* (2013.01);
(Continued)

(58) Field of Classification Search
CPC ...... H01M 4/60; H01M 4/368; H01M 8/0239; H01M 8/188; C07D 209/36; C07D 209/04
(Continued)

(56) References Cited

U.S. PATENT DOCUMENTS 8,080,327 B1     12/2011   Rasmussen
2009/0053578 A1*  2/2009   Isomura .................. C08J 5/2275
                                                              429/413
(Continued)

FOREIGN PATENT DOCUMENTS

DE     10 2012 015176 A1    2/2014
WO     WO 2014/052682 A2    4/2014
WO     WO-2016156451 A1 *  10/2016 .............. H01M 8/00

OTHER PUBLICATIONS

Machine translation of DE 102012015176 (no date).*
(Continued)

*Primary Examiner* — Amanda C. Walke
(74) *Attorney, Agent, or Firm* — Wolf, Greenfield & Sacks, P.C.

(57) ABSTRACT

The present invention relates to an organic flow cell battery having a material comprising an organic molecule that can be used as the electroactive redox material for both electrodes of the battery. By enabling two-electron processes both of the oxidation and reduction to occur in a single molecule, a total of 4-electron transitions is achieved, which allows the organic molecule to be used on both sides of the separator, reducing material costs and allowing the battery to be charge in either direction with equal ease.

7 Claims, 1 Drawing Sheet

(51) Int. Cl.
  *C07D 209/36* (2006.01)
  *H01M 8/18* (2006.01)
  *H01M 4/36* (2006.01)
  *H01M 8/0239* (2016.01)

(52) U.S. Cl.
  CPC ......... *H01M 4/368* (2013.01); *H01M 8/0239* (2013.01); *H01M 8/188* (2013.01); *Y02E 60/528* (2013.01)

(58) Field of Classification Search
  USPC ....................................................... 429/105
  See application file for complete search history.

(56) References Cited

U.S. PATENT DOCUMENTS

| | | | | |
|---|---|---|---|---|
| 2014/0370403 A1* | 12/2014 | Narayan | ............... | H01M 8/188 429/418 |
| 2015/0236543 A1* | 8/2015 | Brushett | ............... | H02J 7/0052 429/81 |
| 2015/0243991 A1* | 8/2015 | Huskinson | ........ | H01M 8/04186 429/72 |
| 2016/0116430 A1* | 4/2016 | Nauber | ............. | G01N 27/4045 205/780.5 |
| 2018/0079721 A1* | 3/2018 | Armand | .................. | H01M 8/00 |
| 2018/0097249 A1* | 4/2018 | Narayan | ............... | H01M 8/188 |

OTHER PUBLICATIONS

Invitation to Pay Additional Fees dated Mar. 16, 2016 for Application No. PCT/EP2015/002607.

International Search Report and Written Opinion dated Sep. 8, 2016 for Application No. PCT/EP2015/002607.

Huskinson et al., A metal-free organic-inorganic aqueous flow battery. Nature. Jan. 9, 2014;505(7482):195-8. Methods. 12 pages.

Roessler et al., Direct Electrochemical Reduction of Indigo: Process Optimization and Scale-Up in a Flow Cell. J Appl Electrochem. Jun. 1, 2002;32(6):647-51.

* cited by examiner

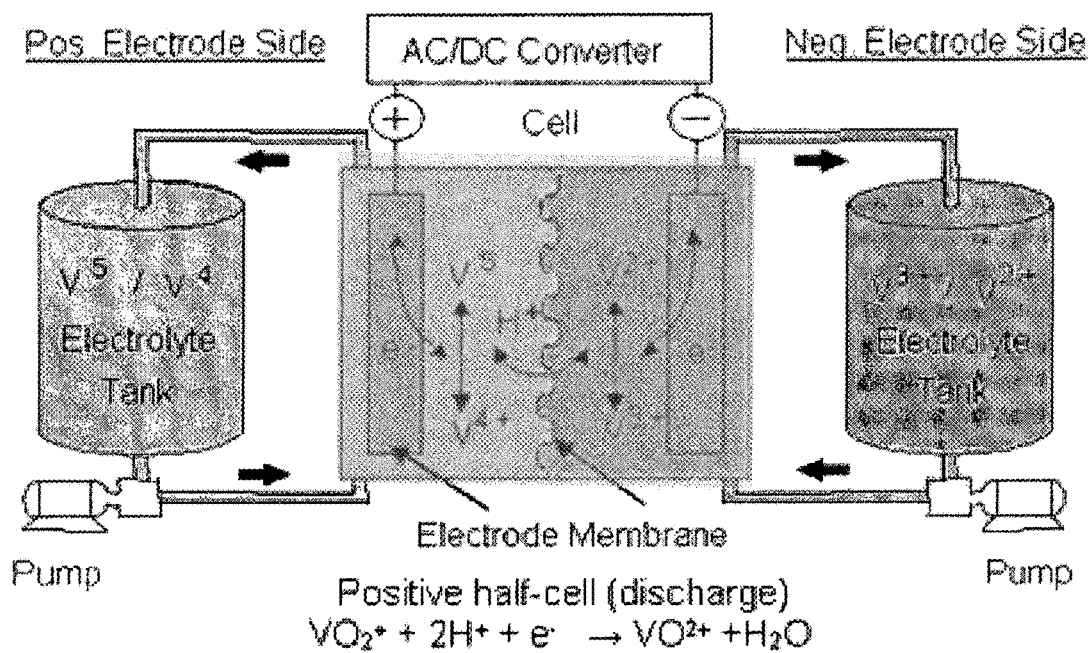

ORGANIC FLOW CELL BATTERIES AND MATERIALS FOR USE IN SAME

RELATED APPLICATIONS

This application is a national stage filing under 35 U.S.C. § 371 of international PCT application, PCT/EP2015/002607, filed Dec. 23, 2015, which claims the benefit under 35 U.S.C. § 119(e) of U.S. Provisional Application Ser. No. U.S. 62/095,832, filed Dec. 23, 2014, each of which is incorporated herein by reference in its entirety.

FIELD OF INVENTION

The present invention relates to organic flow cell batteries and materials for use in organic flow cell batteries. In particular the invention provides examples of organic redox materials for use in flow cell batteries as substitutes for toxic and/or expensive inorganic redox materials such as vanadium salts or bromine.

BACKGROUND OF THE INVENTION

Redox flow cells are secondary batteries in which all electrochemical components are dissolved in the electrolyte.

The energy capacity of the redox flow cell is independent of its power, as the energy available only depends on the electrolyte volume (amount of liquid electrolyte), whereas the power depends on the surface area of the electrodes.

A well-established example is the vanadium redox flow battery, which contains redox couples entirely based on vanadium cations (see FIG. 1). Typical performance data are shown in Tab. 1:

TABLE 1

| Vanadium redox battery performance. | |
|---|---|
| Specific Energy | 10-20 Wh/kg (36-72 J/g) |
| Energy Density | 15-25 Wh/L (54-65 kJ/L) |
| Charge/Discharge Efficiency | 75-80%< |
| Time Durability | 10-20 years |
| Cycle Durability | >10,000 cycles |
| Nominal Cell Voltage | 1.15-1.55 V |

The following half-cell reactions occur in all-vanadium flow cells:

(anode side)

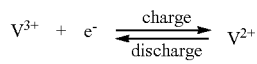

$$V^{3+} + e^- \xrightleftharpoons[\text{discharge}]{\text{charge}} V^{2+}$$

(cathode side)

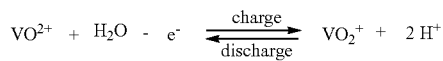

$$VO^{2+} + H_2O - e^- \xrightleftharpoons[\text{discharge}]{\text{charge}} VO_2^+ + 2H^+$$

Although the vanadium redox flow battery is well established, there are a wide range of less commonly used inorganic flow cell chemistries, including the polysulfide-bromide battery (PSB):

(cathode side)

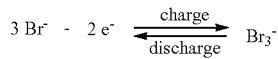

$$3Br^- - 2e^- \xrightleftharpoons[\text{discharge}]{\text{charge}} Br_3^-$$

(anode side)

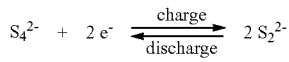

$$S_4^{2-} + 2e^- \xrightleftharpoons[\text{discharge}]{\text{charge}} 2S_2^{2-}$$

The wide-scale utilization of flow batteries is presently limited by the availability and cost of the redox materials, in particular those that are based on redox-active transition metals such as vanadium, and/or require precious-metal electrocatalysts.

A metal-free organic-inorganic aqueous flow battery which combines a quinone/hydroquinone redox couple with a $Br_2/Br^-$ redox couple has been recently proposed by Huskinson et al., Nature 505, 195-198. Herein, bromine is used herein as oxidiser, in combination with the reduced (hydroquinone) form of 9,10-anthraquinone-2,7-disulphonic acid acting as reductant.

However, the toxicity of inorganic redox materials such as vanadium salts or bromine limits the applicability of flow batteries for energy storage in the context of distributed, modular energy generation technologies that use (intermittent) "green power" such as wind, photovoltaic, or hydroelectric power.

In view of the above, the development of new organic redox materials, which offer the prospects of low material costs and reduced toxicity of the energy storage materials would be desirable.

The simplest form of a battery requires a single-electron redox process on both sides of an ion-permeable membrane. This can also be done with organic molecules through the use of stabilised radicals, but in general organic radicals are either relatively chemically reactive or require so much stabilisation that it is difficult to generate the high redox potentials required for a significant cell voltage.

While single-electron transfer materials (e.g. triazine) have been considered, they involve limitations in that they only comprise one electron per molecule.

Molecules such as the quinones have two electron transfers and can therefore have twice the energy density (per mass/volume/cost). Moreover, two-electron processes prevent the necessity of forming unpaired electrons (radicals) in organic molecules, and can readily be accommodated by changing the α- and π-bonds into a different oxidation state. Two-electron processes can therefore be advantageous for enhancing both the stability and the cell potential of a battery system.

To achieve high potentials it is desired that the charged battery should contain a reduced compound and an oxidised compound that are both relatively reactive compared to the uncharged system. It is this electrochemical reaction between the two materials that drives the battery process and the flow of electrons around the external circuit. As long as side reactions do not occur that reduce the lifetime of the compounds, it is preferable to have the highest compound reactivity possible to thereby enable the highest cell potential.

One solution is to take two similar moieties—for example, two different quinones (see e.g. WO 2014/052682 A2)—that have different redox potentials. However, this process makes it difficult to produce high cell potentials due to the relative similarity of the compounds—within one class it is unlikely that both the oxidised form of one and the reduced form of the other will have high reactivity. Therefore, the generally preferred approach is to optimise both molecules independently to achieve the desired high reactivity.

However, leakage of the redox materials through the separator membrane has been identified as being a cause of device degradation, as the available volume of redox active material is slowly reduced and there is also the potential for unwanted reactions to occur between the different redox active materials.

In view of the above, there remains a need for novel organic electroactive redox materials which are readily available and exhibit reduced toxicity and excellent energy density. Moreover, it is desirable to provide organic flow cell batteries that have a high operating potential, high cell output voltage, long lifetime and that may be produced at favourably low costs.

SUMMARY OF THE INVENTION

The present invention solves this object with the subject matter of the claims as defined herein. The advantages of the present invention will be further explained in detail in the section below and further advantages will become apparent to the skilled artisan upon consideration of the invention disclosure.

In its most general form, the present invention relates to an organic flow cell battery having a material comprising an organic molecule that can be used as the electroactive redox material for both electrodes of the battery. By enabling two-electron processes both of the oxidation and reduction to occur in a single molecule, a total of 4-electron transitions is achieved, which allows the organic molecule to be used on both sides of the separator, reducing material costs and allowing the battery to be charge in either direction with equal ease.

Preferred embodiments of the organic flow cell battery according to the present invention and other aspects of the present invention are described in the following description and the claims.

BRIEF DESCRIPTION OF THE DRAWING

FIG. 1 schematically illustrates the configuration of a conventional all-vanadium flow cell.

DETAILED DESCRIPTION OF THE INVENTION

For a more complete understanding of the present invention, reference is now made to the following description:

The present invention has been made upon studying two-electron processes which prevent the necessity of forming unpaired electrons (radicals) in organic molecules, and can readily be accommodated by changing the α- and π-bonds into a different oxidation state and can therefore be advantageous for enhancing both the stability and the cell potential of a battery system.

One requirement of any battery system is for an ion to pass through the separating membrane to compensate for the electron movement through the external circuit. Ions can be positive or negative, but some of the most common include $H^+$, $Li^+$, $Na^+$, $Mg^{2+}$. Coordination of these ions can be used to stabilise the organic molecules, particularly in their reduced states. This is particularly helped when atoms that enhance this coordination are available—typical atoms include O, N, S but can also include P, Se, Te and others.

Typical organic redox processes can then take place, as for example in the classic anthraquinone reduction-oxidation:

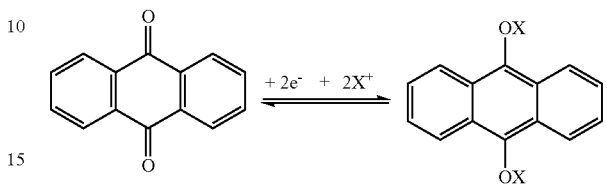

In this case, O is used as the binding atom and X is typically H or Li. Li is a more reactive system and generally requires a non-protic solvent, but this process allows higher voltages (>1.5V) to be achieved without the risk of the $H^+ \leftrightarrow H_2$ reduction taking place.

To achieve high potentials it is desired that the charged battery should contain a reduced compound and an oxidised compound that are both relatively reactive compared to the uncharged system. It is this electrochemical reaction between the two materials that drives the battery process and the flow of electrons around the external circuit. As long as side reactions do not occur that reduce the lifetime of the compounds, it is preferable to have the highest compound reactivity possible to thereby enable the highest cell potential.

One approach to increasing chemical potential (reactivity) is to remove aromatic stabilisation energy in the more reactive form. This is seen with the quinone compound class where the oxidised species of the redox pair is the more chemically reactive as it does not have the aromatic stabilisation.

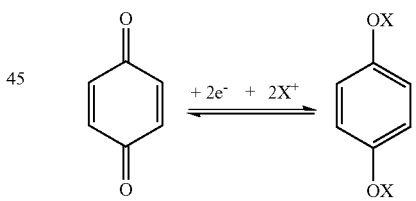

It can be noted that this reactivity in the oxidised form is achieved by having the C=O bonds attached directly to the aromatic ring.

Similar methods can be used to achieve higher reactivity with reduced species, though in this case C=O need to be attached in the benzylic positions:

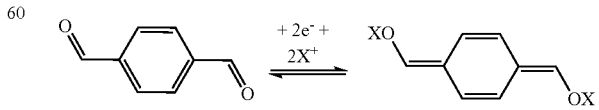

Combining both of these reactions together achieves a relatively large cell output voltage:

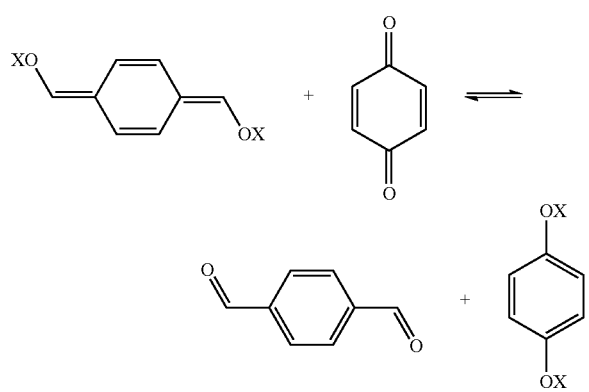

In this case both of the more reactive non-aromatic compounds are on the left in the 'charged' form of the battery, with the less reactive 'non-charged' forms on the right.

However, as has been explained above, the use of two different classes of redox active organic materials in so-called asymmetrical flow cell batteries involves disadvantages, such as e.g. device degradation by leakage through the separator membrane.

The present invention overcomes these obstacles by providing an organic flow cell battery, wherein an organic molecule may be used as the electroactive redox material for both electrodes of the battery, i.e. a symmetrical flow cell battery.

The use of the same material on both sides of the separating membrane enables advantages in terms of cost and battery lifetime.

The organic molecules used in the organic flow cell battery of the present invention are generally characterised in that can be used as both the redox materials at the same time, by having 2×2-electron redox processes enabled within the same molecule. By having 2×2-electron oxidation or reduction processes, wherein both the oxidised and reduced states are relatively electrochemically reactive with respect to the neutral ground state, batteries with higher operating potential may be achieved.

The organic molecules are preferably designed to be stable in the central redox state so both the oxidised and reduced forms are higher in energy—thus generating a higher operating voltage.

In particular, it is preferable that the oxidised and reduced forms are both electrochemically reactive, but the central 'neutral' state is not. This allows the same compound to be used on both sides of the separator, reducing material costs (since only one material needs to be used in the manufacture, for example) and allowing the battery to be charge in either direction with equal ease.

These materials provide improved stability and safety: In an asymmetric flow battery, in the event of any of the redox molecules migrating through the separator membrane there could be chemical incompatibility between the two molecules that could lead to reactions that reduce the safety and/or effectiveness of the battery system—for example by reducing the charge storage ability. These issues are substantially removed by the use of a symmetric battery with the same material for both redox materials. Any material leakage that does occur through the membrane would, in an asymmetric device, reduce the volume of available active material, but in this invention the battery can be charged periodically in the opposite direction so that any leakage effects are reversed, thus prolonging the battery's useful lifetime.

Molecules can be chosen to have these desired redox characteristics—some examples are given in the table below:

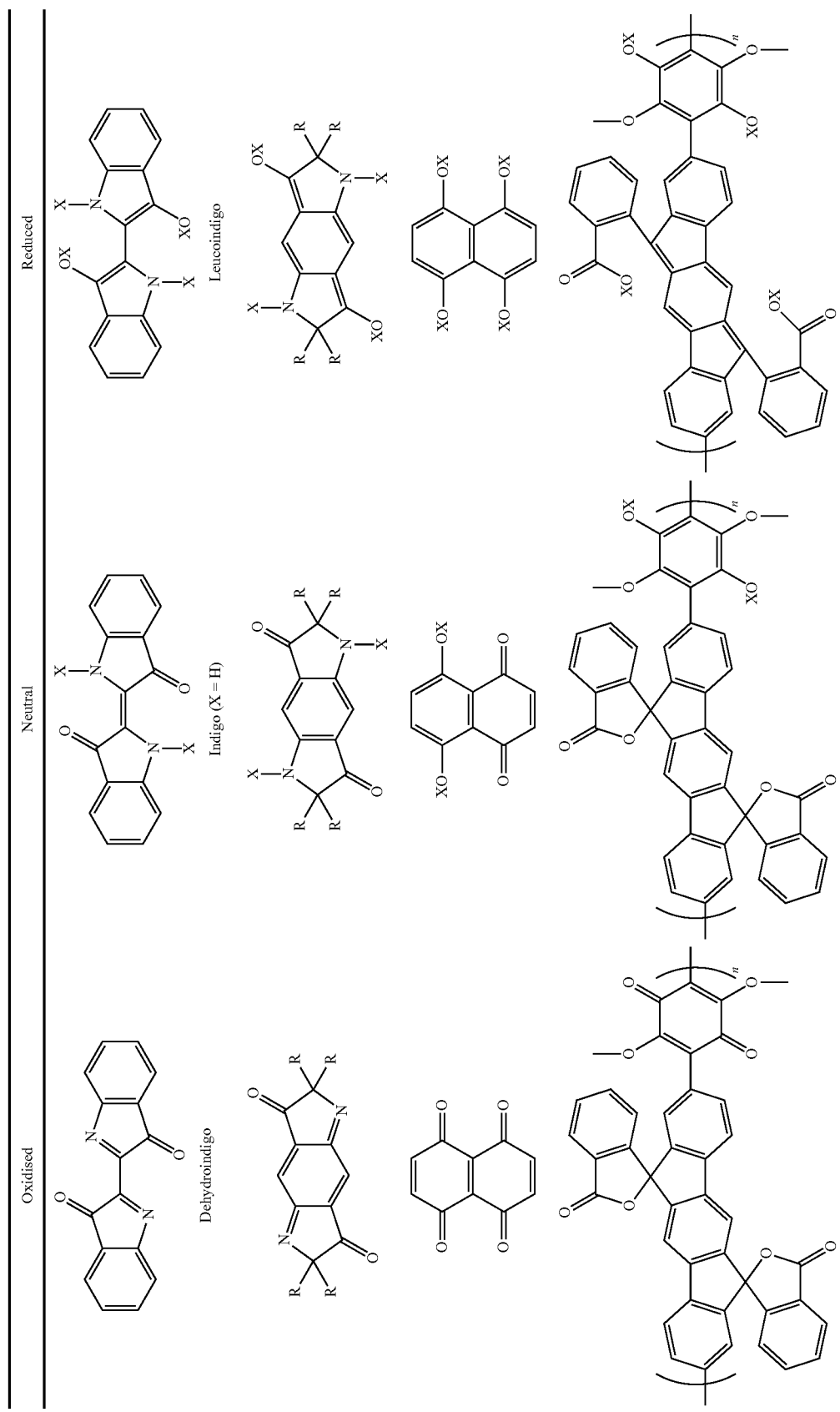

-continued
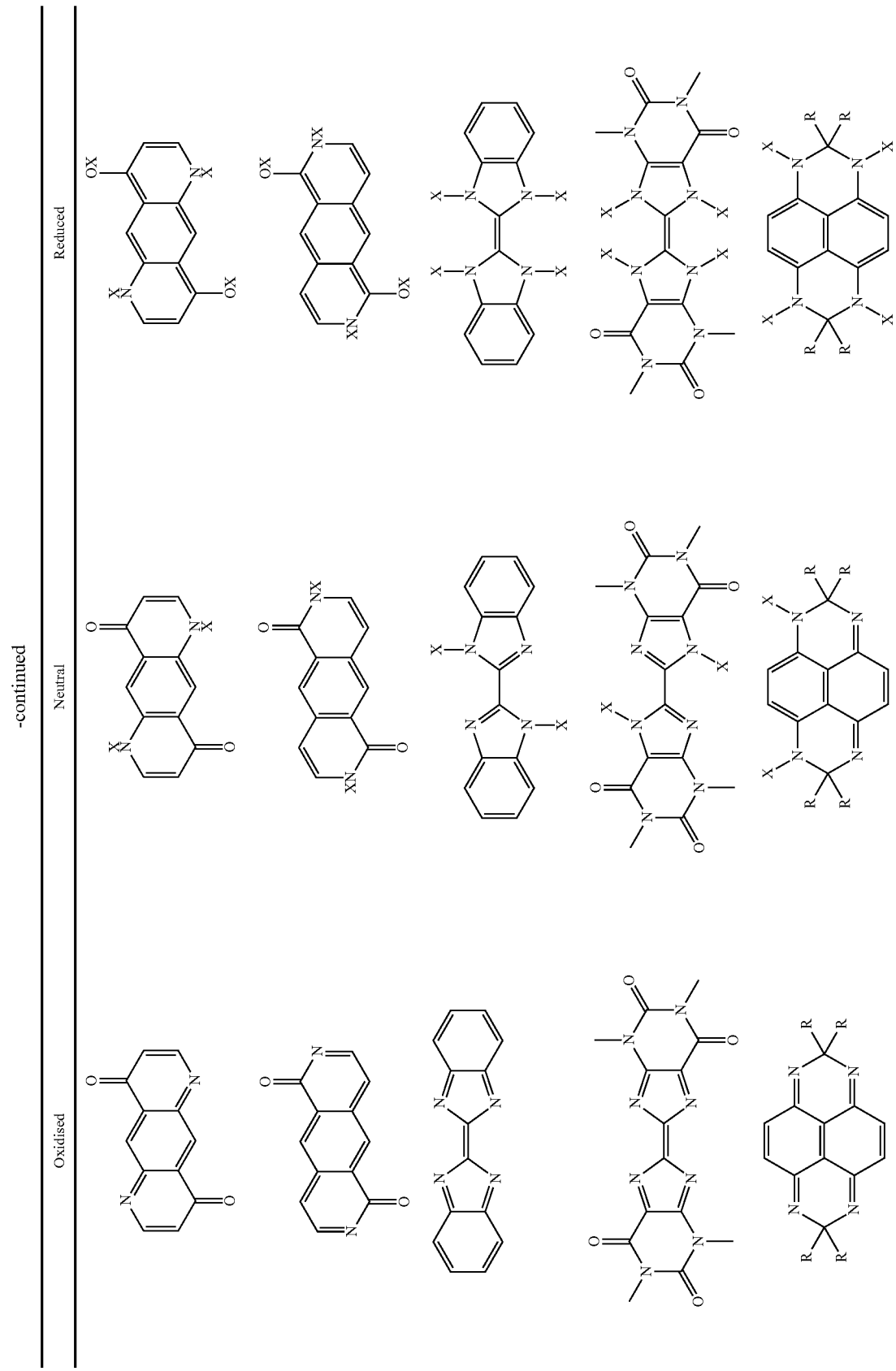

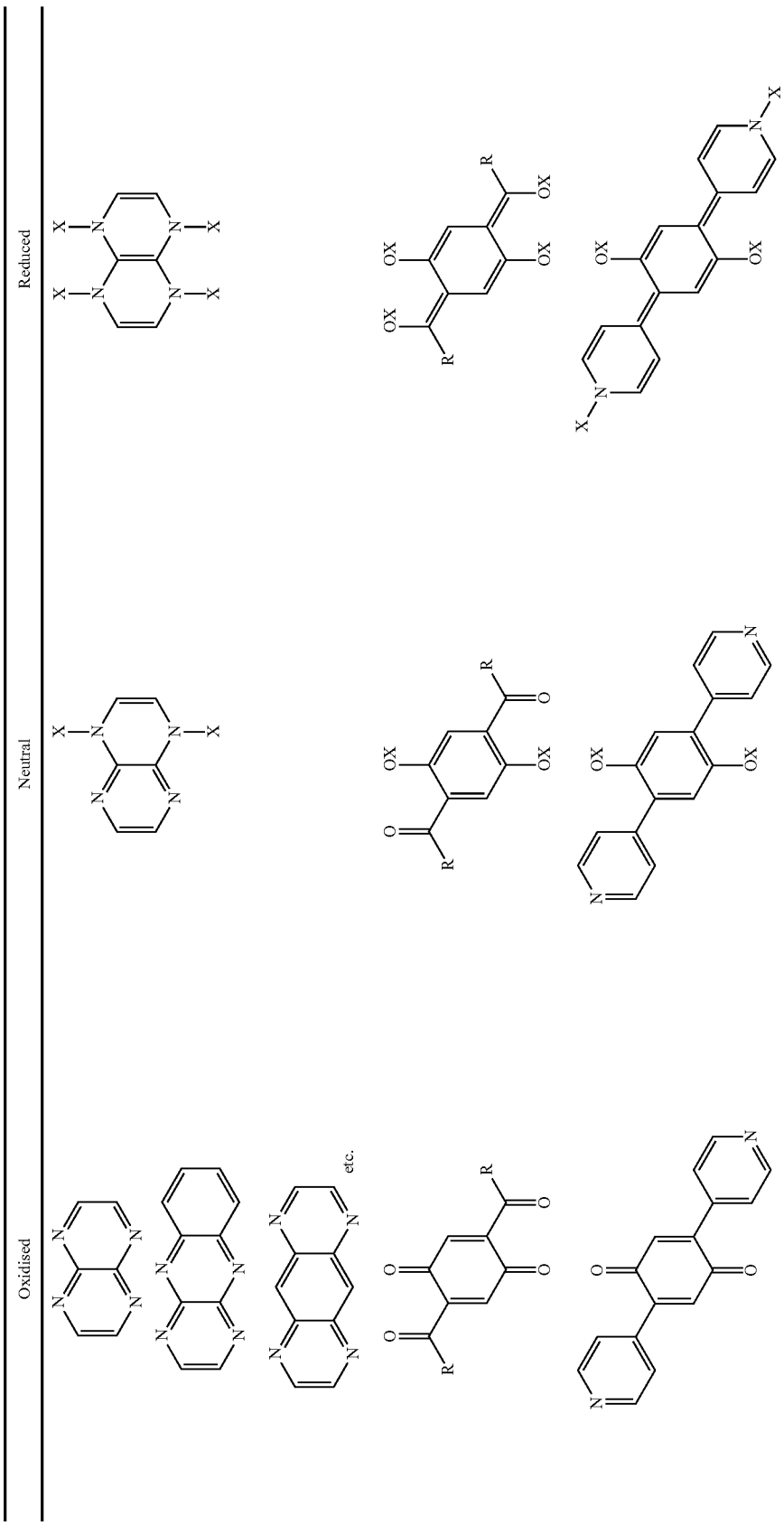

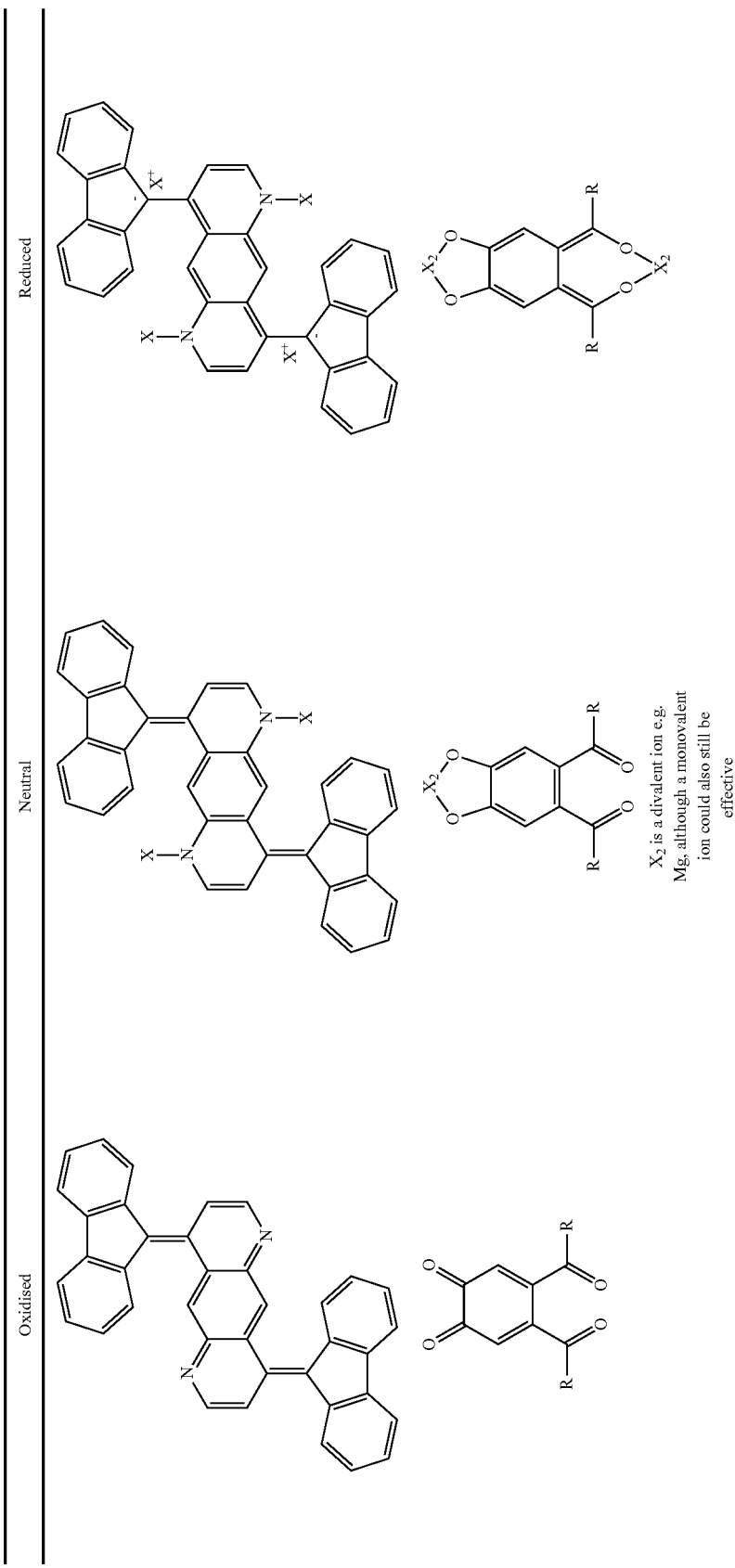

The core units (active molecules) shown in the above table can be unsubstituted or substituted with solubilizing groups. As examples of solubilizing groups, sulfonate groups, linear or branched $C_1$-$C_6$ alkyl groups, linear or branched $C_1$-$C_6$ halogenoalkyl groups and linear or branched $C_1$-$C_6$ alkoxy groups may be mentioned. Preferably, the solubilizing group is a sulfonate group.

In the core units listed above, R is selected from any one of a substituted or unsubstituted $C_1$-$C_{12}$ alkyl group or a substituted or unsubstituted aryl group. In case the groups are substituted, the substituent is preferably selected from a halogen, a $C_1$-$C_6$ alkyl group, or a $C_6$-$C_{12}$ aryl group. As examples of unsubstituted $C_1$-$C_{12}$ alkyl groups or an unsubstituted aryl group, methyl, n-butyl, and phenyl groups may be mentioned.

The generic X in the above table denotes a proton, a tetraalkylammonium ion, an alkali metal ion, or an alkaline earth metal ions. Preferably, X is any one selected from the group consisting of $H^+$, $Li^+$, $Na^+$, or $Mg^{2+}$.

In a preferred embodiment, X is $Li^+$, used in combination with a non-protic solvent, which allows higher voltages (>1.5V) to be achieved.

Preferably the core units do not comprise pyrazine-based cyanoazacarbons.

A preferred example organic molecule constituting the electroactive redox material is the molecule indigo and its substituents, that can be reduced to leucoindigo or oxidised to dehydroindigo, along with corresponding movements of ions ($H^+$, $Li^+$, $Na^+$ etc.) and electrons.

The present electrical storage device preferably uses a single ion-transporting membrane. As an alternative, two ion transporting membranes with a reservoir of electrolyte in between could be used, as is described in U.S. Pat. No. 8,080,327.

Rather than being uncharged in its central 'relaxed' redox state, the molecule in the present invention is already partially charged and already has counter-charges (either coordinating such as $H^+$ or $Li^+$ or non-coordinating such as $R_4N^+$). These same ions can then move from the cathode side to the anode side as the battery is charged, in an electrically driven disproportionation process, for example:

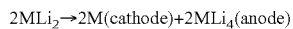

$$2MLi_2 \rightarrow 2M(\text{cathode}) + 2MLi_4(\text{anode})$$

where M is the organic molecule in question.

It is important to note that the molecule needs to be carefully selected to ensure that both oxidation and reduction processes are energetically demanding, and can therefore provide an effectively high potential difference when charged.

Methods to improve the chemical stability of the system (as opposed to the electrochemically desired reactions) can include: a) the use of substitutions to affect the steric and/or electronic reactivity, and b) choice of different electroactive groups. For example, the carbonyls illustrated above could be replaced with cyclic or non-cyclic imines or other hetero-nitrogen compounds.

Increasing the solubility of the molecules can increase the working concentration of the active material, reducing solvent costs and increasing the energy density per unit volume/weight. Depending on the molecules, solvents and electrolytes being considered, various different solubilising groups can be added to the active molecule to increase the solubility in all of the required oxidation states. Alkyl groups, whether straight-chained or branched, can enable solubilisation in less-polar solvents such as xylene, while adding more polar functionalities such as ether, polyether or ester groups can increase the solubility in higher polarity solvents. Where possible, the simplest possible solubilising group (if any) would be used so as to minimise the costs of the battery system.

For an effective battery technology, the precise molecules along with their substitutions should be chosen so as to reduce the unwanted side reactions below what would affect the desired battery lifetime.

In a preferred embodiment, the organic molecule constituting the electroactive redox material is not a quinone.

The electrolyte used in the organic flow cell battery of the present invention is not particularly limited as long as it is electrochemically stable under operating conditions and has a electrochemical window within the operating voltage range. As typical examples, organic electrolytes such as tetraethylammonium hexafluorophosphate or inorganic electrolytes such as sodium chloride may be mentioned, depending on the solvent being used and the electrochemical window. Further possibilities include the use of known ionic liquids. As an example of the latter, N-methyl-N-butylpyrrolidonium bis(trifluoromethylsulfonyl)imide may be mentioned.

Electrode materials can be made from any conducting material that is chemically and electrochemically stable under the operating conditions. The surface of the electrode is all that needs to have this stability, and the electrode can be made of more than one material as long as any incompatible materials are thoroughly covered by the inert conducting material. Examples of inert materials include materials such as gold, platinum or carbon.

The separator materials may likewise be suitably chosen by the skilled artisan from separator materials known in the art as long as they are fully inert to the environment and do not, for example, dissolve in the solvent or electrolyte. As examples for a separator material, ion-conductive membranes may be mentioned, of which Nafion is a well-known example for transporting protons. However, the separator membranes which may be used in the present invention are not only limited to ion-conductive material but may also include highly porous membranes, such as cellulose-based separator membranes.

The present invention provides different possibilities for tuning the organic flow cell battery depending on the desired purpose.

For example, the flow cell battery may be configured so as to reduce its production costs while still maintaining a good efficiency.

In this context, the separator membrane has been identified as a key material as it defines the performance and economic viability of the redox flow cell batteries, particularly as it may contribute to a large portion of the overall battery system costs. In asymmetric devices, the choice and quality of the separator membrane is crucial under aspects of battery efficiency and lifetime (i.e. leakage prevention).

Advantageously, by using the same material for both redox active components the present invention allows a much wider choice of membrane materials. For example, it is not necessary to use an ion-selective membrane in order to achieve a satisfactory device performance, but it may be sufficient to use a low-cost porous separator membrane. For example, by adjusting a relatively high flow rate and ensuring that the discharge onto the electrode is faster than the diffusion rate through the separator, inexpensive microporous or even porous filter paper may be used without severely impairing the device efficiency.

As a preferred inexpensive example of an indigo derivative which may be used as the organic molecule constituting the electroactive redox material, indigo-5,5'-disulfonic acid disodium salt (indigo carmine) may be mentioned, a commercially available water-soluble food dye:

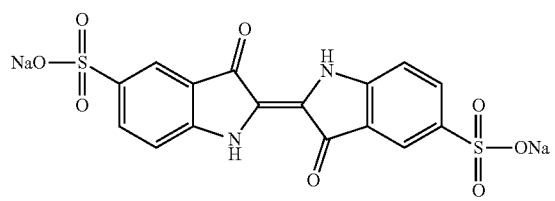

In combination with an aqueous electrolyte comprising an inexpensive salt (e.g. sodium chloride) and a weak acid for proton conductivity, an organic redox flow cell battery may be manufactured extremely cost-effectively.

Given the above disclosure, many other features, modifications, and improvements will become apparent to the skilled artisan.

The invention claimed is:

1. An organic flow cell battery having a material comprising an organic molecule that is the electroactive redox material for both electrodes of the battery, wherein the organic molecule is present in the organic flow cell battery in three different oxidation states, wherein both an oxidized and reduced state of the organic molecule are electrochemically reactive with respect to a neutral ground state, and the organic molecule has a core unit of formula:

| Oxidized |
| --- |

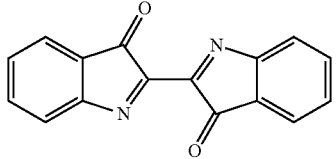 [SMILES: O=C1C(C2=Nc3ccccc3C2=O)=Nc2ccccc21]

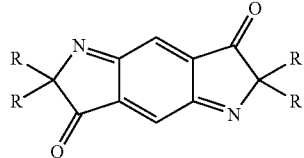

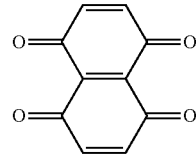

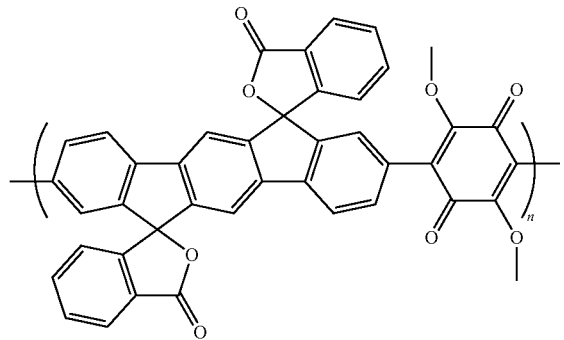

-continued

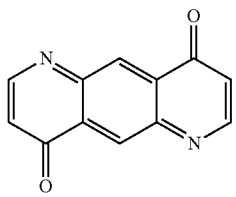 [SMILES: O=C1C=CN=c2cc3c(cc21)=NC=CC3=O]

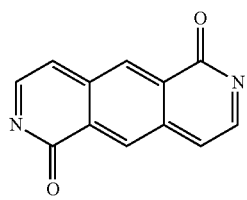 [SMILES: O=C1N=CC=c2cc3c(cc21)=CC=NC3=O]

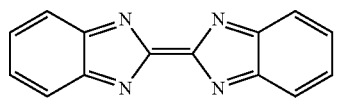 [SMILES: c1ccc2c(c1)=NC(=C1N=c3ccccc3=N1)N=2]

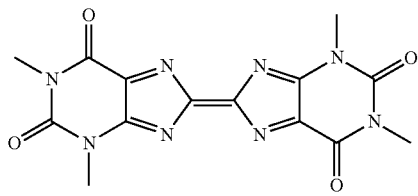

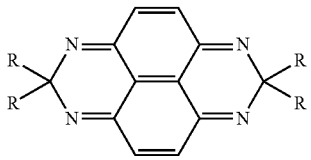

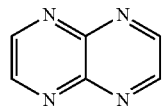

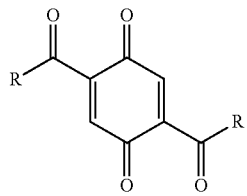

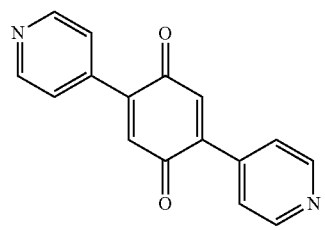 [SMILES: O=C1C=C(c2ccncc2)C(=O)C=C1c1ccncc1]

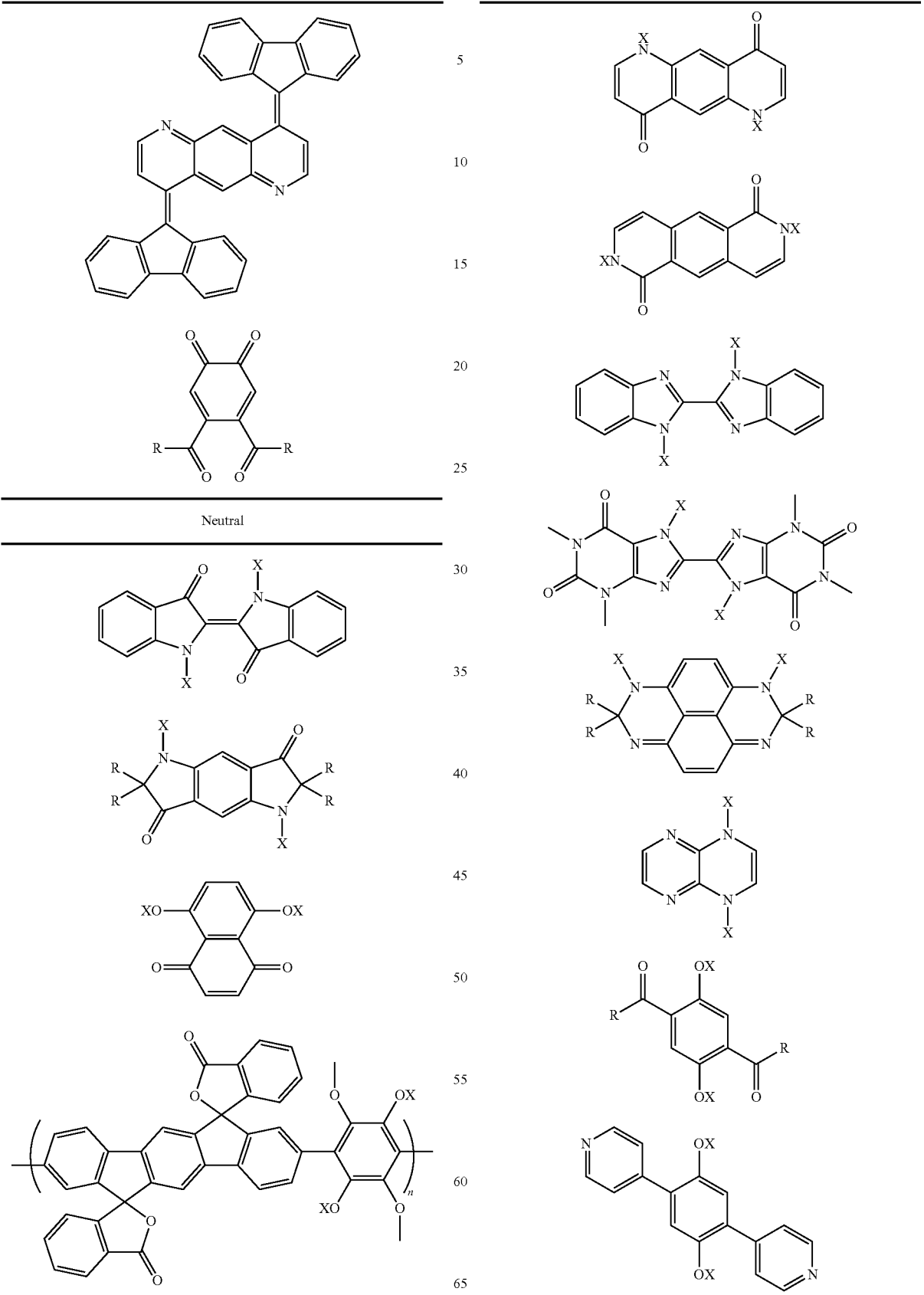

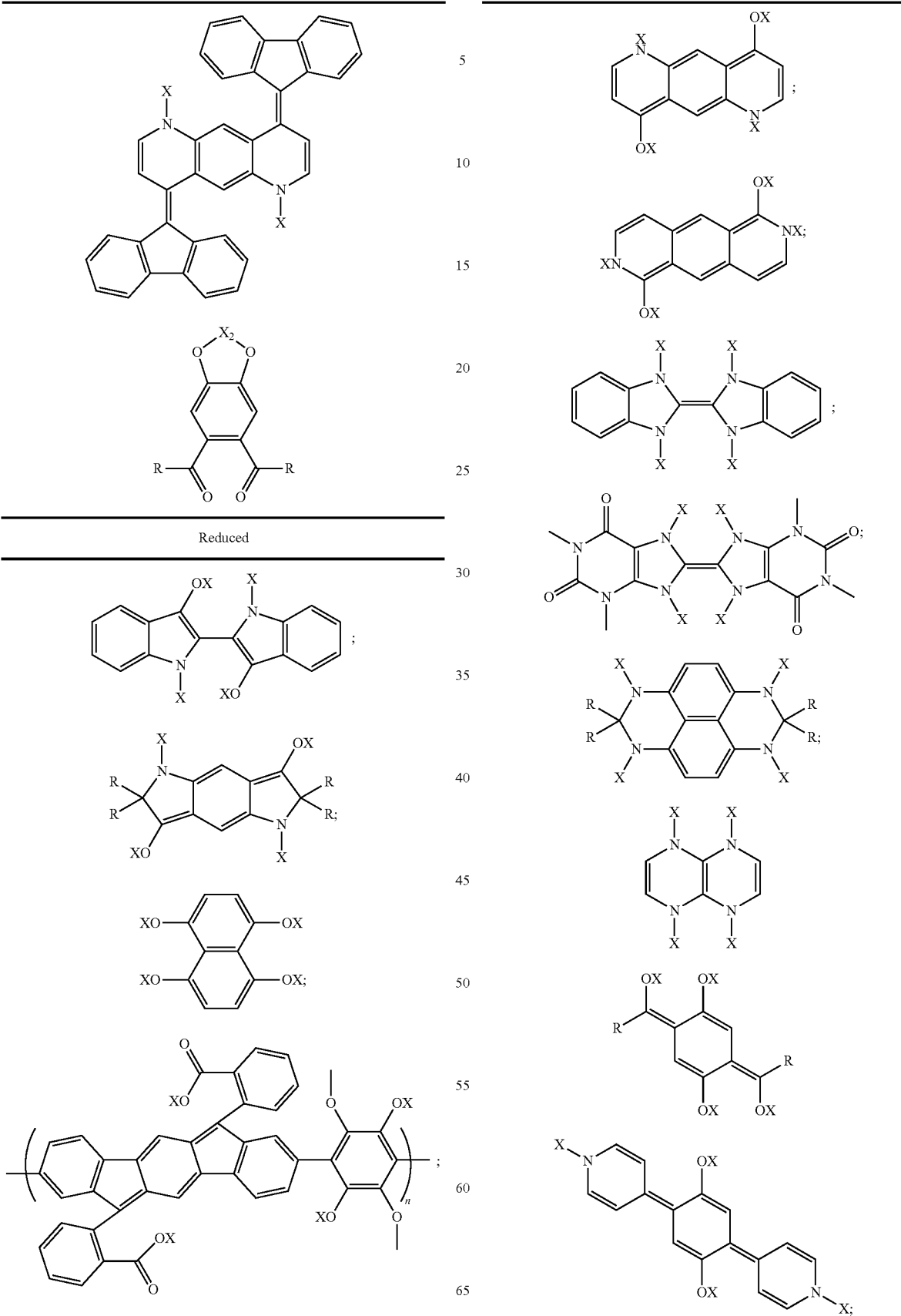

-continued

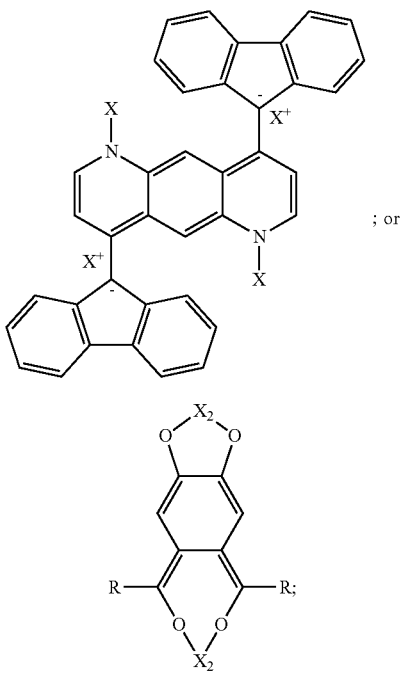

wherein X is H⁺, Li⁺, Na⁺ or Mg²⁺;
X₂ is a divalent ion; and
R is a substituted or unsubstituted $C_1$-$C_{12}$ alkyl group or a substituted or unsubstituted aryl group.

2. The organic flow cell battery according to claim 1, wherein the core units are substituted with a solubilizing group selected from a sulfonate group, a linear or branched $C_1$-$C_6$ alkyl group, a linear or branched $C_1$-$C_6$ halogenoalkyl group, and a linear or branched $C_1$-$C_6$ alkoxy group.

3. The organic flow cell battery according to claim 2, wherein the solubilizing group is a sulfonate group.

4. The organic flow cell battery according to claim 1, wherein the organic molecule in its neutral form is indigo or a derivative thereof.

5. The organic flow cell battery according to claim 1, wherein the organic molecule in its neutral form is indigo-5,5'-disulfonic acid disodium salt:

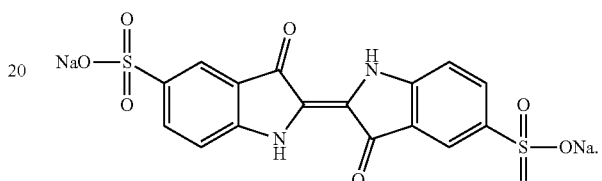

6. The organic flow cell battery according to claim 1, further comprising a porous separator membrane.

7. The organic flow cell battery according to claim 6, wherein the porous separator membrane consists of porous or microporous filter paper.

* * * * *